United States Patent [19]

Mathew

[11] Patent Number: 5,162,566
[45] Date of Patent: Nov. 10, 1992

[54] STEREOSPECIFIC SYNTHESIS OF TETRASUBSTITUTED ACRYLIC ESTERS

[75] Inventor: Jacob Mathew, Fenton, Mo.

[73] Assignee: Mallinckrodt Specialty Chemicals Company, St. Louis. Mo.

[21] Appl. No.: 749,853

[22] Filed: Aug. 26, 1991

[51] Int. Cl.$^5$ .............................................. C07C 69/76
[52] U.S. Cl. ........................................ 560/104; 560/8
[58] Field of Search ........................... 560/104, 8, 205

[56] References Cited

U.S. PATENT DOCUMENTS 4,980,377 12/1990 Lafon .................................. 514/649

OTHER PUBLICATIONS

Hudrilik et al., Sterospecific Olefin-Forming Elimination Reactions of β-Hydroxylalkylsilanes, *J. Am. Chem. Soc.*, vol. 97, pp. 1464–1468 (1975).
Posner et al., Alkylation of Enolate Ions Generated Regiospecifically via Organocopper . . . Systems, *J. Am. Chem. Soc.* vol. 97, pp. 107–118 (1975).
J. Mathew, A Novel Route to Substituted Cyclopent-2-3n-1-one; Application to . . . Dihydrojasmone, *J. Chem. Soc. Chem. Com.*, pp. 684–686 (1990).
Peterson, A Carbonyl Olefination Reaction Using Silyl-Substituted Organometallic Compounds, *J. Org. Chem.*, vol. 33, pp. 780–784 (1968).
Jacob Mathew, Synthesis and recations of . . . and Novel Cyclopentenones, *J. Org. Chem.* vol. 55, pp. 5294–5297 (1990).
Jacob Mathew, Synthesis and Reactions of a α--Chloro-,βc-unsaturated Esters, *J. Org. Chem.*, vol. 55, pp. 3880–3386 (1990).
Goering, Alkylation of Allylic Derivatives . . . Lithium Dialkylcuprates, *J. Org. Chem.*, vol. 48, pp. 715–721 (1983).
Underiner et al., Cross Coupling of Allylic Derivatives . . . Phenylcooper Reagents, *J. Org. Chem. Soc.* vol. 54, pp. 3239–3240 (1989).
Fox, Technically Speaking, *Cosmetics & Toiletries*, vol. 102, pp. 21–24 (1987).
Gage, J. R. and Evans D. A., *Organic Synthesis*, vol. 68 pp. 77, 83 (1989).
Erickson, T. J., "Asymmetric Synthesis of Darvon Alcohol," *J. Org. Chem., vol. 51, pp. 934–935 (1986)*.
Pohland, A. and Sullivan, H. R., *J. Am. Chem. Soc.*, vol. 77, p. 3400.
Evans, D. A. et al., Stereoselective Aldol Condensations via Boron Enolates, *J. Am. Chem. Soc.*, vol. 103, pp. 3099–3111 (1981).
Parikh, J. R. and Doering, W., *J. Am. Chem. Soc.* vol. 89, pp. 5505–5507 (1967).
Pohland, et al., *J. Org. Chem.*, vol. 28, p. 2483 (1963).
Brown and Devant, *Tetrahedron Letters*, 25:5031–5034 (1984).
Evans et al., *J. Am. Chem. Soc.* pp. 103:2999–3111 (1981).

Primary Examiner—Paul J. Killos
Attorney, Agent, or Firm—Rothwell, Figg, Ernst & Kurz

[57] ABSTRACT

Substantially stereospacific (E)-tetrasubstituted acrylic esters, such as

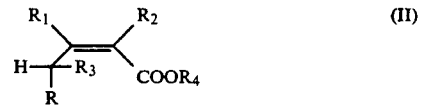

(II)

where R is hydrogen alkyl, $R_1$ is alkyl, aryl or aralkyl, $R_2$ and $R_4$ are alkyl, are formed from racemic mixtures of corresponding unsaturated esters and cuprates of the formula $(R_3)_2CuX$, wherein $R_3$ is alkyl, aryl or aralkyl, and X is lithium or magnesium halide.

19 Claims, No Drawings

STEREOSPECIFIC SYNTHESIS OF TETRASUBSTITUTED ACRYLIC ESTERS

BACKGROUND OF THE INVENTION

1. Field of the Invention

The present invention relates generally to methods for producing tetrasubstituted acrylic esters.

2. Description of the Background Art

Acrylic esters can be used as intermediates in many different and varied organic synthesis procedures in which compounds which possess particular qualities and characteristics can be produced. In particular, stereospecific acrylic esters can be especially useful as intermediates in these organic synthesis procedures.

For example, an (E)-tetrasubstituted acrylic ester of the formula

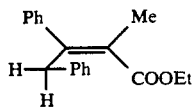 (E)

where Ph represents a phenyl group, Me represents a methyl group, and Et represents an ethyl group, can be converted into d-Oxyphene as taught by Erickson, T. J., *J. Org. Chem.*, Vol. 51, p. 934–5 (1986). The compound d-Oxyphene, in turn, can be converted into d-propoxyphene, a compound which possesses good analgesic qualities. Pohland, A., and Sullivan, H. R., *J. Am. Chem. Soc.*, Vol. 77, p. 3400 (1955).

Furthermore, (E)-tetrasubstituted acrylic esters can be converted into 2,3 disubstituted-2-cyclopenten-1-ones. Mathew, J., *J. Org. Chem.*, Vol. 55, p. 5294–5297 (1990); Mathew, J., *J. Chem. Soc. Chem. Commun.*, p. 684–6 (1990). These cyclopentenones are valuable in the perfume and pharmaceutical industries.

Accordingly, it is desirable to synthesize (E)-tetrasubstituted acrylic esters in high yield and with good stereospecificity so that these esters can be used as intermediates in the synthesis of compounds such as d-propoxyphene and cyclopentenones.

Organic synthesis of tetrasubstituted acrylic esters can occur through a number of different reaction mechanisms or routes. Among these mechanisms or routes are the Wittig reaction (Wadsworth, W. J., *Organic Reactions*, Chp. 2, p. 73–253 (1977)) and the Peterson reaction (Hudrlik, P., and Peterson, D., *J. Am. Chem. Scc.*, Vol. 97, p. 1464 (1975)). The Wittig reaction comprises reacting a phosphorane with a compound containing a carbonyl group so as to obtain an unsaturated compound. The Peterson reaction is essentially an elimination reaction in which β-hydroxyalkylsilanes are reacted with metallic hydrides (e.g., diisobutylaluminum hydride) to produce an olefin.

Previously, methods in which olefins have been synthesized, such as the Wittig and Peterson reactions, have yielded tetrasubstituted olefins with poor stereospecificity. Therefore, methods are needed for synthesizing stereospecific tetrasubstituted acrylic esters quickly, efficiently and with good stereospecificity.

SUMMARY OF THE INVENTION

In accordance with the present invention, a method for producing a substantially stereospecific tetrasubstituted acrylic ester, comprises reacting an unsaturated ester of the formula

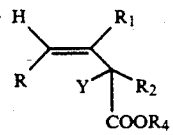 (I)

with a cuprate of the formula $(R_3)_2CuX$ so as to obtain an (E)-tetrasubstituted acrylic ester

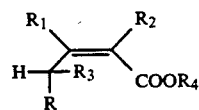 (II)

wherein R is hydrogen or an alkyl group of from 1 to about 10 carbon atoms. $R_1$ is an alkyl group of from 1 to about 10 carbon atoms, an aryl group containing from about 6 to about 10 carbon atoms which may be unsubstituted or substituted by one or more alkyl groups of from 1 to about 10 carbon atoms, or an aralkyl group wherein the alkyl portion contains from 1 to about 10 carbon atoms and the aryl portion contains from about 6 to about 10 carbon atoms, which aryl portion can be unsubstituted or substituted by one or more alkyl groups of from 1 to about 10 carbon atoms. $R_2$ is an alkyl group of from 1 to about 10 carbon atoms. Y is halogen. $R_3$ is an alkyl group of from 1 to about 10 carbon atoms, an aryl group of from about 6 to about 10 carbon atoms which may be unsubstituted or substituted by one or more alkyl groups of from 1 to about 10 carbon atoms, or an aralkyl group wherein the alkyl portion contains from 1 to about 10 carbon atoms and the aryl portion contains from about 6 to about 10 carbon atoms, which aryl portion can be unsubstituted or substituted by one or more alkyl groups of from 1 to about 10 carbon atoms. $R_4$ is an alkyl group of from 1 to about 10 carbon atoms. X is lithium or magnesium halide.

DETAILED DESCRIPTION OF THE PREFERRED EMBODIMENTS

The present invention is applicable to unsaturated esters of the formula (I) above, and may comprise a racemic mixture thereof.

R is hydrogen or an alkyl group of from 1 to about 10 carbon atoms, which may be straight chain or branched. In preferred embodiments, R is hydrogen or an alkyl group of from 1 to about 5 carbon atoms, more preferably, hydrogen or an alkyl group of from 1 to about 3 carbon atoms, and most preferably hydrogen or methyl.

In accordance with one embodiment, $R_1$ is an alkyl group of from 1 to about 10 carbon atoms, which may be straight chain or branched. In embodiments wherein $R_1$ is an alkyl group, it is preferably an alkyl group of from 1 to about 5 carbon atoms, more preferably, from 1 to about 3 carbon atoms, and most preferably a methyl or an ethyl group.

In accordance with another embodiment, $R_1$ is an aryl group containing from about 6 to about 10 carbon atoms, such as phenyl or naphthyl. An aryl $R_1$ may be unsubstituted or substituted by 1 or more alkyl groups of from 1 to about 10 carbon atoms. Alkyl substituent(s) of Aryl $R_1$ may be straight chain or branched, and in preferred embodiments, contain from 1 to about 5 carbon atoms, more preferably from 1 to about 3 carbon atoms, and most preferably are methyl or ethyl.

In still another embodiment, $R_1$ can be an aralkyl group wherein the alkyl portion is straight chain or branched and contains from 1 to about 10 carbon atoms. In preferred embodiments, when $R_1$ is an aralkyl group, the alkyl portion contains from 1 to about 5 carbon atoms, more preferably from 1 to about 3 carbon atoms, and most preferably, 1 or 2 carbon atoms. When $R_1$ is aralkyl, the aryl portion can contain from about 6 about 10 carbon atoms. An aryl portion of aralkyl $R_1$ can be unsubstituted, or substituted by one or more alkyl groups of from 1 to about 10 carbon atoms, preferably from 1 to about 5 carbon atoms, more preferably from 1 to about 3 carbon atoms, and most preferably 1 or 2 carbon atoms.

$R_2$ is an alkyl group of from 1 to about 10 carbon atoms, which can be straight chain or branched. In preferred embodiments, $R_2$ is an alkyl group of from 1 to about 5 carbon atoms, more preferably from 1 to about 3 carbon atoms, and most preferably methyl or ethyl.

Y represents halogen, such as chlorine, bromine or iodine. In preferred embodiments, Y is chlorine or bromine, and, in particularly preferred embodiments, Y is chlorine.

$R_4$ is an alkyl group of from 1 to about 10 carbon atoms, and can be straight chain or branched. In preferred embodiments, $R_4$ contains from 1 to about 5 carbon atoms, more preferably from 1 to about 3 carbon atoms, and most preferably is methyl or ethyl.

Unsaturated esters of the formula (I) can be produced by methods which are known in the art. For example, an unsaturated ester of the formula (I) wherein R is hydrogen, $R_1$ is phenyl, $R_2$ is methyl, $R_4$ is ethyl and Y is chlorine can be synthesized by reacting triethyl phosphonopropionate with acetophenone using sodium hydride in the presence of hexane and THF to yield a reaction product, which is then reacted with calcium hypochlorite and acetic acid in the presence of water and methylene chloride at ice bath temperature. Mathew, J., *J. Org. Chem.*, Vol. 55, p. 3880 (1990).

In accordance with the present invention, the unsaturated ester of formula (I) is reacted with a cuprate of the formula $(R_3)_2CuX$. In accordance with one embodiment, $R_3$ is an alkyl group of from 1 to about 10 carbon atoms which can be straight chain or branched. In preferred embodiments, alkyl $R_3$ contains from 1 to about 5 carbon atoms, more preferably from 1 to about 3 carbon atoms, and most preferably is methyl or butyl.

In accordance with another embodiment, $R_3$ is an aryl group of from 6 to about 10 carbon atoms which may be unsubstituted, or substituted by 1 or more alkyl groups of from 1 to about 10 carbon atoms, which can be straight chain or branched. In preferred embodiments, alkyl substituent(s) of aryl $R_3$ contain from 1 to about 5 carbon atoms, more preferably from 1 to about 3 carbon atoms, and most preferably are methyl or ethyl.

In yet another embodiment, $R_3$ is an aralkyl group wherein the alkyl portion is straight chain or branched and contains from 1 to about 10 carbon atoms, preferably from 1 to about 5 carbon atoms, more preferably from 1 to about 3 carbon atoms, and most preferably 1 or 2 carbon atoms. When $R_3$ is aralkyl, the aryl portion contains from about 6 to about 10 carbon atoms, and such aryl portion can be unsubstituted, or substituted by 1 or more straight chain or branched alkyl groups of from 1 to about 10 carbon atoms. When the aryl portion of $R_3$ is substituted, in preferred embodiments, such substituant(s) contain from 1 to about 5 carbon atoms, more preferably from 1 to about 3 carbon atoms, and most preferably are methyl or ethyl.

X is lithium or magnesium halide. The halide portion can be, for example, chloride, bromide or iodide, and in preferred embodiments, is bromide.

The dialkyl or diaryl cuprate of the formula $(R_3)CuX$, where $R_3$ and X are defined as before, can be synthesized by any suitable methods. For example, these cuprates can be produced by reacting CuI with a compound of the formula $R_3X$, where $R_3$ and X are defined as before, in a non-polar solvent, such as tetrahydrofuran (THF) or a THF/hexane mixture, at ice bath temperature. Posner, G., et al., "Alkylation of Enolate Ions Generated Regiospecifically via Organocopper Reactions. Synthesis of Decalin Sequiterpene Valerane and of Prostaglandin Model Systems," *J. Am. Chem Soc.*, Vol. 97, p. 107 (1975). These dialkyl and diaryl cuprates appear to attack the unsaturated ester in a regioselective manner, i.e., the cuprates do not attack the ester carbonyl, whereas organolithium or sodium compounds do exclusive carbonyl attack. Mathew, J., *J. Org Chem.*, Vol. 55, p. 3880 (1990); Mathew, J., *J. Org. Chem.*, Vol. 55, p. 5294 (1990). This regioselective attack appears to allow the cuprates to introduce an alkyl or an aryl group to the unsaturated ester so as to control the ester's stereospecificity.

Suitable cuprates for use in accordance with the present invention include dialkyl or diaryl alkaline-cuprates such as $(Ph)_2CuLi$ or $(n-Bu)_2CuLi$, and dialkyl or diaryl alkaline earth metal halide-cuprates such as $(Ph)_2CuMgBr$ or $(n-Bu)_2CuMgBr$. The cuprate can be reacted with the unsaturated ester of formula (I) in the presence of a non-polar solvent such as tetrahydrofuran (THF), hexane, or a mixture thereof.

Advantageously, the unsaturated ester is reacted with the cuprate at a temperature of about 0° C., e.g., in an ice bath.

As set forth above, the unsaturated ester of formula (I) is reacted with the previously described cuprate, so as to form an (E)-tetrasubstituted acrylic ester of the formula (II) set forth above.

The present invention has been utilized to provide substantially pure stereospecific acrylic esters. For example, an unsaturated ester of the formula (I) wherein R is H, $R_1$ is phenyl, $R_2$ is methyl, $R_4$ is ethyl and Y is chloro, has been reacted with a cuprate of the formula $(Ph)_2CuMgBr$ in the presence of THF and hexane at ice bath temperature, so as to form an (E)-tetra-substituted acrylic ester, (E)-3,4-diphenyl-2-methyl-2-butenoic acid, ethyl ester in substantially 100% purity.

The invention having been generally described, the following examples are given as particular embodiments of the invention and to demonstrate the practice and advantages thereof. It is to be understood that the examples are given by way of illumination and are not intended to limit the specification or the claims in any way.

EXAMPLE 1

Triethyl Phosphonopropionate: Ethyl bromopropionate (92 g 0.5 mole) and triethyl phosphite (83 g, 0.5 mole) were stirred and heated to about 200° C. under a air cooled reflux condenser. The ethyl bromide that was evolved was collected with the aid of a cooling trap. After 1 hour of heating the pot temperature went up to 230° C. At this point the evolution of ethyl bromide ceased. The yellow oil was cooled to room temperature (RT) and then distilled under vacuum. There was obtained 112 g of phosphonate (93%) boiling at 105°/20 mm Hg as a colorless oil.

EXAMPLE 2

Ethyl 2-Methyl-3-Phenyl-2-Butenoate: The above phosphonate (24 g, 0.1 mole) of THF(30 ml) was added dropwise to a cooled stirred suspension of 97% NaH (2.6 g, 0.1 mole) in Hexane (100 ml) and THF (10 ml) under Nitrogen. There was vigorous evolution of hydrogen gas. After the addition the clear yellow tan solution was stirred at RT for 30 minutes. At this point dimethylformamide (DMF) (20 ml) was added followed by acetophenone (11 g, 95 m.mole) in hexane (1 0ml). The resulting yellow brown solution was stirred at 40° C. or 24 hours and then worked up with water (40 ml) and ether (100 ml). The organic layer was separated, washed with water (2×10 ml), dried over MgSO4 and evaporated to give yellow oil. The oil was filtered over silica gel (100 g) and washed with hexane (150 ml). The hexane was removed and the resulting oil distilled under vacuum. There was obtained (16 g, 78%) of the cinnamate esters as a mixture of E and Z isomers. (66:34) boiling at 110° C./2 mm Hg.

EXAMPLE 3

Ethyl 2-Chloro-2-Methyl-3-Phenyl-3-butenoate (1): To a stirred solution of the above ester (10 g, 50 m.mole) in methylene chloride (250 ml) was added Ca(OCl)$_2$ (5.6 g, 40 m.mole) and ice water (25 ml). The two phase solution was cooled to 0° C. and glacial acetic acid (3.6 g, 60 m.mole) was added dropwise in 5 minutes. The cloudy reaction mixture was then stirred for 1 hour at ice-bath temperature and quenched with water (20 ml) and methylene chloride (40 ml). The organic layer was separated, washed with water (2×10 ml), aq.NaHCO$_3$ (2×20 ml) and dried over anhydrous MgSO$_4$ and CaCl$_2$. Evaporation gave pale yellow viscous oil. This was filtered over silica gel (50 g) and washed with hexane. The hexane elutes were evaporated to give the allylic halide (1) (11 g, 91%) as a colorless viscous oil. $^1$H NMR: δ 7.25(s, 5H), 6.05 (s, 1H), 5.85 (s, 1H), 4.10 (q, 2H), 1.95 (s, 3H) and 1.20 (t, 3H).

EXAMPLE 4

(E)-3,4-Diphenyl-2-Methyl-2-Butenoic Acid, Ethyl Ester: To a stirred solution of CuI (2 g, 10 m.mole) in THF (30 mL) under nitrogen at ice-bath temperature was added a 1M solution of PhMgBr in THF (20 ml, 20. mole) slowly via syringe. The deep black brown solution was stirred for 1 hour at RT and then recooled with ice. A solution of ester (1)(2.4 g, 10 m.mole) in THF (5 ml) and hexane (15 ml) was then added via syringe in the course of 1 minute. The brown green solution stirred at RT for 2 hours and worked up by diluting with ether (20 ml) and saturated ammonium chloride (15 ml). The mixture was filtered through celite and washed with THF. The organic layer was separated and washed with 1N HCl (20 ml), brine (10 ml), aq.-sodium thiosulfate (2×10 ml) and dried over Magnesium sulfate. Evaporation gave the crude ester as a yellow oil. Flash column chromatography on solica gel gave pure E Ester as a colorless oil (2.5 g, 89%) eluting in hexane. $^1$H NMR (60 MHz, CDCl$_3$): δ 1.30 (3H,t), 1.75 (3H.s), 3.90 (3H,s), 4.20 (2H,q), 6.85-7.35 (10H,m); IR (neat) 3060, 3020, 2980, 1710, 1625, 1600, 1490, 1250 cm$^{-1}$; C—13NMR: δ 169.94, 146.78, 141.12, 138.63, 129.15, 128.04, 126.93, 126.84, 125.90, 60.51, 41.82, 17.55, 14.24.

EXAMPLE 5

The procedures set forth in examples 1-4 were generally applied to react unsaturated esters of the formula (I) with cuprates of the formula (R$_3$)$_2$CuX, having the components set forth in Table I, below, to form tetrasubstituted acrylic esters of the formula (II) having the components set forth in Table II below, wherein Me is methyl, Ph is phenyl, Et is ethyl, and n-Bu is n-butyl.

TABLE I

| (STARTING MATERIAL COMPONENTS) | | | | | | |
|---|---|---|---|---|---|---|
| Reaction # | R | R$_1$ | R$_2$ | R$_4$ | Y | R$_3$ | X |
| 1 | H | Me | Me | Et | Cl | Ph | Li |
| 2 | H | Me | Me | Et | Cl | n-Bu | Li |
| 3 | H | Ph | Me | Et | Cl | Ph | Li |
| 4 | H | Et | Me | Et | Cl | Ph | Li |
| 5 | Me | Ph | Me | Et | Cl | Ph | Li |

TABLE II

| (FINAL PRODUCT) | | | | | | | |
|---|---|---|---|---|---|---|---|
| Compound | R | R$_1$ | R$_2$ | R$_3$ | R$_4$ | Yield % | E-isomer % | Z-isomer % |
| A | H | Me | Me | Ph | Et | 90 | 92 | 8 |
| B | H | Me | Me | n-Bu | Et | 87 | 90 | 10 |
| C | H | Ph | Me | Ph | Et | 89 | 100 | 0 |
| D | H | Et | Me | Ph | Et | 91 | 94 | 6 |
| E | Me | Ph | Me | Ph | Et | 82 | 90 | 10 |

What is claimed is:
1. A method for producing a substantially stereospecific tetrasubstituted acrylic ester which comprises reacting an unsaturated ester of the formula

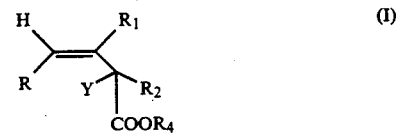

with a cuprate of the formula (R$_3$)$_2$CuX so as to obtain an (E)-tetrasubstituted acrylic ester,

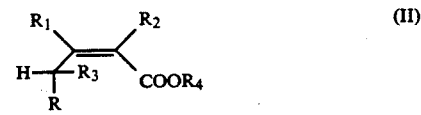

wherein R is hydrogen or an alkyl group of from 1 to about 10 carbon atoms; R$_1$ is an alkyl group of from 1 to about 10 carbon atoms, an aryl group containing from about 6 to about 10 carbon atoms which may be unsubstituted or substituted by one or more alkyl groups of from 1 to about 10 carbon atoms, or an aralkyl group wherein the alkyl portion contains from 1 to about 10 carbon atoms and the aryl portion contains from about 6 to about 10 carbon atoms, which aryl portion can be unsubstituted or substituted by one or more alkyl groups of from 1 to about 10 carbon atoms; R$_2$ is an alkyl group of from 1 to about 10 carbon atoms; Y is halogen; R$_3$ is an alkyl group of from 1 to about 10 carbon atoms, an aryl group of from about 6 to about 10 carbon atoms which may be unsubstituted or substituted by one or more alkyl groups of from 1 to about 10 carbon atoms, or an aralkyl group wherein the alkyl portion contains from 1 to about 10 carbon atoms and the aryl portion contains from about 6 to about 10 carbon atoms, which aryl portion can be unsubstituted or substituted by one or more alkyl groups of from 1 to about 10 carbon atoms; $R_4$ is an alkyl group of from 1 to about 10 carbon atoms; and X is lithium or magnesium halide.

2. The method of claim 1 wherein R is hydrogen.

3. The method of claim 1 wherein R is a methyl group.

4. The method of claim 1 wherein $R_1$ is a methyl or an ethyl group.

5. The method of claim 1 wherein $R_1$ is a phenyl group.

6. The method of claim 1 wherein $R_2$ is a methyl group.

7. The method of claim 1 wherein Y is chlorine.

8. The method of claim 1 wherein $R_4$ is an ethyl group.

9. The method of claim 1 wherein $R_3$ is a phenyl group.

10. The method of claim 1 wherein $R_3$ is an n-butyl group.

11. The method of claim 1 wherein X is lithium.

12. The method of claim 1 wherein X is magnesium bromide.

13. The method of claim 1 wherein R is hydrogen, $R_1$ is a phenyl group, $R_2$ is a methyl group, Y is chlorine, $R_3$ is a phenyl group, $R_4$ is an ethyl group, and X is lithium or magnesium bromide.

14. The method of claim 1 wherein the reaction between the unsaturated ester and the cuprate occurs at about 0° C.

15. The method of claim 1 wherein the reaction between the unsaturated ester and the cuprate occurs in the presence of tetrahydrofuran and hexane.

16. The method of claim 1 wherein the reaction between the unsaturated ester and the cuprate occurs in the presence of the non-polar solvent.

17. The method of claim 16 wherein the non-polar solvent is selected from the group consisting of tetrahydrofuran, hexane, and a mixture thereof.

18. The method of claim 17 wherein said reaction occurs at a temperature of about 0° C.

19. A method for producing a substantially stereospecific tetrasubstituted acrylic ester which comprises reacting in a non-polar solvent at about 0° C., an unsaturated ester of the formula

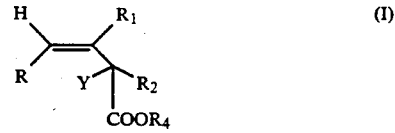

with a cuprate of the formula $(R_3)_2CuX$ so as to obtain an (E)-tetrasubstituted acrylic ester,

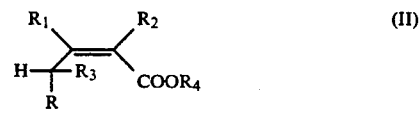

wherein R is hydrogen or an alkyl group of from 1 to about 10 carbon atoms; $R_1$ is an alkyl group of from 1 to about 10 carbon atoms, an aryl group containing from about 6 to about 10 carbon atoms which may be unsubstituted or substituted by one or more alkyl groups of from 1 to about 10 carbon atoms, or an aralkyl group wherein the alkyl portion contains from about 1 to about 10 carbon atoms and the aryl portion contains from about 6 to about 10 carbon atoms, which aryl portion can be unsubstituted or substituted by one or more alkyl groups of from 1to about 10 carbon atoms; $R_2$ is an alkyl group of from 1 to about 10 carbon atoms; Y is halogen; $R_3$ is an alkyl group of from 1 to about 10 carbon atoms, an aryl group of from about 6 to about 10 carbon atoms which may be unsubstituted or substituted by one or more alkyl groups of from 1 to about 10 carbon atoms, or an aralkyl group wherein the alkyl portion contains from 1 to about 10 carbon atoms and the aryl portion contains from about 6 to about 10 carbon atoms, which aryl portion can be unsubstituted or substituted by one or more alkyl groups of from 1 to about 10 carbon atoms; $R_4$ is an alkyl group of from 1 to about 10 carbon atoms; and X is lithium or magnesium halide.

* * * * *

UNITED STATES PATENT AND TRADEMARK OFFICE
CERTIFICATE OF CORRECTION

PATENT NO. : 5,162,566
DATED : November 10, 1992
INVENTOR(S) : Jacob Mathew

It is certified that error appears in the above-indentified patent and that said Letters Patent is hereby corrected as shown below:

Col. 3, line 8, after "about 6" insert -- to --; Col. 4, line 63, "a" should be -- an --; Col. 5, line 14, replace "(1 oml)" with -- (10 ml) --.

Signed and Sealed this

Twenty-ninth Day of March, 1994

Attest:

BRUCE LEHMAN

*Attesting Officer*  *Commissioner of Patents and Trademarks*